(12) United States Patent
Karol et al.

(10) Patent No.: US 6,489,484 B1
(45) Date of Patent: Dec. 3, 2002

(54) THIADIAZOLE ADDITIVES AND LUBRICATING COMPOSITIONS CONTAINING THE SAME

(75) Inventors: Thomas J. Karol, Norwalk, CT (US); Ronald J. Tepper, Fairfield, CT (US)

(73) Assignee: R. T. Vanderbilt Company, Inc., Norwalk, CT (US)

(*) Notice: Subject to any disclaimer, the term of this patent is extended or adjusted under 35 U.S.C. 154(b) by 89 days.

(21) Appl. No.: 09/693,220

(22) Filed: Oct. 20, 2000

Related U.S. Application Data

(60) Provisional application No. 60/160,569, filed on Oct. 20, 1999.

(51) Int. Cl.[7] ..................... C07D 285/13; C10M 135/36
(52) U.S. Cl. ..................... 548/142; 508/231; 508/274
(58) Field of Search ..................... 548/142; 508/231, 508/274

(56) References Cited

U.S. PATENT DOCUMENTS

| | | | |
|---|---|---|---|
| 4,128,510 A | 12/1978 | Richwine | 528/36 |
| 4,301,019 A | 11/1981 | Horodysky et al. | 252/49.6 |
| 4,306,988 A | 12/1981 | Rothgery | |
| 4,410,703 A | 10/1983 | Okorodudu | 548/142 |
| 4,517,103 A | 5/1985 | Hoffman et al. | 252/28 |
| 4,584,114 A | 4/1986 | Gemmill et al. | 252/47.5 |
| 4,908,144 A | 3/1990 | Davis et al. | 252/47.5 |
| 4,910,210 A | 3/1990 | Beriger | 514/363 |
| 4,933,265 A | 6/1990 | Inoue et al. | 430/378 |
| 4,935,157 A | 6/1990 | Karol | 252/47.5 |
| 5,026,865 A | 6/1991 | Karol | 548/142 |
| 5,055,584 A | 10/1991 | Karol | 548/142 |
| 5,102,568 A | 4/1992 | King et al. | 252/47.5 |
| 5,126,397 A | 6/1992 | Horodysky et al. | 252/34 |
| 5,138,065 A | 8/1992 | Karol | 548/125 |
| 5,194,621 A | 3/1993 | Karol et al. | 548/142 |
| 5,217,502 A | 6/1993 | Hsu | 44/331 |
| 5,512,190 A | 4/1996 | Anderson et al. | 252/47 |
| 5,849,925 A | 12/1998 | Karol et al. | 548/142 |

FOREIGN PATENT DOCUMENTS

EP        0 847 998        6/1998

OTHER PUBLICATIONS

T. Liston, et al.; "Engine Lubricant Additives What They are and How They Function"; Journal of the Society of Tribologists and Lubrication Engineers; May 1992; pp. 389–397.

S. Papalardo, et al.; "Synthesis and Structural Aspects of (2,5)–1,3–4–Thiadiazolo and (3,5)–1,3,4–Thiadiazolino Thia Crown Ethers" J. Org. Chem. vol. 52, No. 15, 1987; pp. 3409–3413.

S. Pappalardo et al,; "Chemistry of N–Heterocyclic Sulfur Compounds, Reaction of 2,5–Dimercapto–1,3,4–thiadiazoles with 1, w–Dibromoalkanes, Synthesis of Tetrathia[n+2__.(n__2)](2,5)–1,3,3–thiadiazolophanesand DIthia[(n+1).(n+1)](3,5)–1,3,4–thiadiazolinophanedithiones" J. Org. Chem. vol., 52, No. 3 1987; pp. 405–412.

*Primary Examiner*—Robert Gerstl
(74) *Attorney, Agent, or Firm*—Norris, McLaughlin & Marcus

(57) ABSTRACT

Thiadiazole-poly(ether)glycol reaction products and adducts useful as extreme pressure additives. Lubricating compositions (e.g., greases) containing the reaction products and adducts exhibit improved Timken Load properties.

26 Claims, No Drawings

THIADIAZOLE ADDITIVES AND LUBRICATING COMPOSITIONS CONTAINING THE SAME

This application claims priority under 35 U.S.C. §119(e) from Provisional Application No. 60/160,569, filed Oct. 20, 1999.

FIELD OF THE INVENTION

The present invention relates to 2,5-dimercapto-1,3,4-thiadiazole reaction products and adducts useful as extreme pressure additives, and more particularly to 2,5-dimercapto-1,3,4-thiadiazole/glycol reaction products and adducts useful as extreme pressure additives.

BACKGROUND OF THE INVENTION

A variety of additives are used in lubricants to substantially improve performance. For example, extreme pressure additives are routinely incorporated into an untreated (i.e., base) lubricating composition (e.g., grease) to significantly improve performance. Extreme pressure additives are believed to produce a film on the surface of a metal which can both increase the load carrying capacity of lubricant, and protects the metal surface under high load conditions from deterioration due to wear, welding, and abrasion.

Lead naphthenates and lead -dialkyldithiocarbamates are frequently used as additives to improve the EP performance of greases. However, lead is a heavy metal which is considered "poisonous" in all forms. As an alternative, metal additives (such as antimony, zinc, and bismuth) have been used as a replacement for lead. However, these heavy metals still provide environmental concerns regarding the use. Accordingly, it has long been a goal in the art to develop non-metal lubricating materials to replace heavy metal additives while providing acceptable extreme pressure performance.

The effectiveness of potential extreme pressure additives is conventionally ascertained by the 4-Ball Weld Test (ASTM D-2596) and the Timken Load Test (ASTM D-2509). An ideal candidate compound should exhibit good results in both tests since each test quantitates different extreme pressure properties.

Known to those skilled in the art 2,5-dimercapto-1,3,4-thiadiazole (DMTD) derivatives are effective as anti-wear additives in lubricants. Examples of DMTD derivatives useful as anti-wear additives include the monosulfide and disulfide dimers of DMTD as disclosed in U.S. Pat. Nos. 4,517,103 and 5,194,621, maleate adducts of DMTD as disclosed in U.S. Pat. Nos. 5,102,568, 5,055,584 and 5,138,065 and mono-alkylated and thioacteal derivatives as disclosed in U.S. Pat. No. 5,849,925.

DMTD derivatives are also known to provide good 4-Ball Weld properties. In fact, the 4-Ball Weld properties of DMTD derivatives often exceed commercial requirements. Unfortunately, these same derivatives generally exhibit poor Timken Load performance since the DMTD derivatives do not generally provide Timken Loads levels greater than 35 pounds. As a result, commercialization of DMTD derivatives as extreme pressure additives has been limited.

In view of the above, there exists a need in the art for DMTD derivative that provide both adequate 4-Ball Weld and Timken Load properties. Accordingly, it is an object of the present invention to provide DMTD derivatives that provide adequate 4-Ball Weld and Timnken Load properties, which will allow for the effective utilization of DMTD derivatives as extreme pressure additives.

SUMMARY OF THE INVENTION

The present invention provides 2,5-dimercapto-1,3,4-thiadiazole/glycol reaction products and adducts useful as extreme pressure additives. In one embodiment, an additive is provided including a reaction product of:

(A) a thiadiazole compound having formula (I):

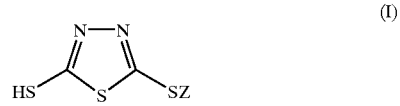

(I)

where Z is a branched or straight chain $C_1$ to $C_{20}$ alkyl radical, a $C_1$ to $C_{20}$ thioalkyl radical, an alpha bound succinate half or full ester, where the ester alkyl is a $C_1$ to $C_5$ alkyl radical, an alkali metal, an alkyloxy linkage having formula (II):

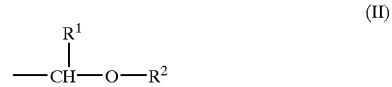

(II)

or combinations thereof, where $R^1$ is hydrogen, a $C_1$ to $C_{20}$ branched or straight chain alkyl radical, a phenyl radical, a $C_1$ to $C_{20}$ branched or straight chain alkyl-substituted-phenyl radical, or combinations thereof and $R^2$ is hydrogen, a $C_1$ to $C_{20}$ branched or straight chain alkyl radical, a phenyl radical, a $C_1$ to $C_{20}$ branched or straight chain alkyl-substituted-phenyl radical, or combinations thereof; and (B) a poly(ether)glycol having formula (III):

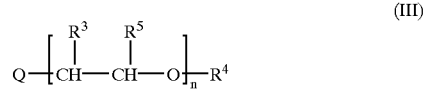

(III)

where Q is a hydroxyl radical, a branched or straight chain $C_1$ to $C_{20}$ alkoxy radical, a branched or straight chain $C_1$ to $C_{20}$ alkoxycarboxyl radical, a mono-substituted, di-substituted, or tri-substituted glycerol residue, hydrogen, or combination thereof; where $R^3$ and $R^5$ are hydrogen, or a methyl radical; where $R^4$ is hydrogen, a branched or straight-chain a $C_1$ to $C_{20}$ alkyl radical, a phenyl radical, a $C_1$ to $C_8$ branched or straight chain alkyl-substituted-phenyl radical, a $C_1$ to $C_{20}$ branched or straight chain acyl radical, or combinations thereof; and where n is 1 to 300.

In another embodiment, the present invention provides an additive including a thiadiazole-glycol adduct having formula (IV):

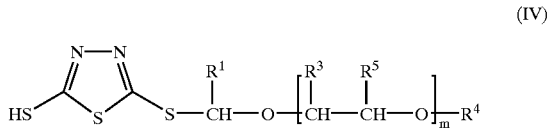

(IV)

where $R^1$ is hydrogen, a branched or straight chain $C_1$ to $C_{20}$ alkyl radical, a phenyl radical, a branched or straight chain $C_1$ to $C_{20}$ alkyl-substituted-phenyl radical or combination thereof; where $R^3$ is hydrogen, a methyl radical, or combinations thereof, where $R^4$ is hydrogen, a $C_1$ to $C_{20}$ branched or straight chain alkyl radical, a phenyl radical, a branched or straight chain $C_1$ to $C_{20}$ alkyl-substituted-phenyl radical, a branched or straight chain $C_1$ to $C_{20}$ acyl radical, or combinations thereof, and where m is from 1 to 50.

Lubricating compositions including the reaction products and adducts of the present invention are also provided. Advantageously, the lubricating compositions of the invention exhibit significantly improved Timken load properties as compared previous DMTD derivatives. These and other advantages of the present invention will be readily apparent from the detailed description set forth below.

DETAILED DESCRIPTION OF THE INVENTION

Present invention provides reaction products and adducts of mono-substituted-2,5-dimercapto-1,3,4-thiadiazole derivatives (hereinafter "thiadiazole compounds") and poly(ether)glycols useful as extreme pressure additives in lubricants. The thiadiazole-glycol reaction products and adducts have unexpectedly been found to provide good Timken Load properties in addition to good 4-Ball Weld properties. Advantageously, the reaction products and adducts provide an alternative to the heavy metal extreme pressure additives commonly used in lubricants.

In one embodiment the present invention provides an additive including a reaction product of a thiadiazole compound and a poly(ether)glycol. The thiadiazole compound is a mono-substituted 2,5-dimercapto-1,3,4-thiadiazole having formula (I):

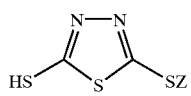
(I)

in which the substituent "Z" is either: (1) a branched or straight chain $C_1$ to $C_{20}$ alkyl radical, with $C_1$ to $C_8$ radical being preferred; (2) a branched or straight chain $C_1$ to $C_{20}$ thioalkyl radical with a $C_1$ to $C_8$ radical being preferred; (3) an alpha bound succinate half or full ester, where the ester alkyl is a $C_1$ to $C_5$ alkyl radical; (4) an alkyloxy linkage having formula (II)

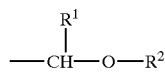
(II)

(5) an alkali metal; or a combination thereof. In this context, "alpha bound" means that the thiadiazole moiety is bound to a carbon atom in an alpha position relative to the carbonyl moiety of the full or partial ester. When Z is an alkyloxy linkage the substituent $R^1$ is either: (1) hydrogen; (2) a branched or straight chain $C_1$ to $C_{20}$ alkyl radical, with a $C_1$ to $C_8$ alkyl radical being preferred; (3) a phenyl radical; (4) a branched or straight chain $C_1$ to $C_{20}$ alkyl-substituted-phenyl radical, with a $C_1$ to $C_8$ alkyl substituent being preferred; or a combination thereof. Likewise, the substituents for $R^2$ are independently chosen from the same group of substituents described for $R^1$. In a preferred embodiment, when Z is an alkyloxy linkage $R_1$ is hydrogen and $R^2$ is a $C_3$ to $C_8$ alkyl radical.

Thiadiazole compounds falling within the above-described parameter are known in the art and are easily synthesized following known techniques. For example, thiadiazole compounds having an alpha bound succinate half or full ester are disclosed in U.S. Pat. No. 5,055,584, which is incorporated herein by reference.

The second component for synthesizing the thiadiazole-glycol reaction product is a poly(ether)glycol having formula (III):

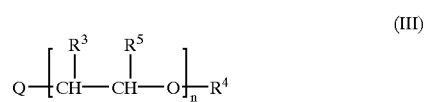

in which Q is either: (1) a hydroxy radical; (2) a branched or straight chain $C_1$ to $C_{20}$ alkoxy radical, with a $C_1$ to $C_{10}$ radical being preferred; (3) a branched or straight chain $C_1$ to $C_{20}$ alkoxycarboxyl radical, with a $C_1$ to $C_{10}$ radical being preferred; (4) a mono-substituted, di-substituted, or tri-substituted glycerol residue; (5) hydrogen; or a combination thereof. The substituents $R^3$ and $R^5$ are either: hydrogen; or a methyl radical. The substituent $R^4$ is either: (1) hydrogen; (2) a branched or straight chain $C_1$ to $C_{20}$ alkyl radical, with a $C_1$ to $C_8$ radical being preferred; (3) a phenyl radical; (4) a branched or straight chain $C_1$ to $C_{20}$ alkyl-substituted-phenyl radical, with a $C_1$ to $C_8$ alkyl substituent being preferred; (5) a branched or straight chain $C_1$ to $C_{20}$ acyl radical, with a $C_1$ to $C_{10}$ radical being preferred; or a combination thereof. The number of ether repeating units "n" ranges from 1 to 300, with 1 to 150 being preferred, with 1 to 10 being more preferred.

Poly(ether)glycols falling within the above described parameters are known in the art. Representative examples of the glycols include, but are not limited to, polyethylene glycol, polypropylene glycol, tetraethylene glycol, ethyloxytriethyleneglycol, butoxytriethylene glycol, dimethoxytriethyleneglycol, triethyleneglycol di-nonanoate, butoxytriglycol, and triethyleneglycol dimethylether. One particularly preferred glycol is butoxytriethylene glycol. The glycols are commercial available from a variety of sources. Preferably, the glycols have a molecular weight from 340 to 4000, with 340 to 1000 being preferred. The glycols should have a viscosity less than 4000 centistokes at 25° C. for ease of handling. Likewise, the glycols should have a minimal effect on the dropping point of greases.

The reaction product is formed by combining the two sole components with or without a solvent and subsequently heating the components, if necessary. Preferably, the thiadiazole compound is dispersed in the glycol, which is normally in a liquid state at room temperature. Heating the thiadiazole/glycol mixture is not required when the thiadiazole compound is in a liquid state at room temperature. However, if the thiadiazole compound is in a solid state at room temperature, the mixture may be heated (e.g., to at least 100° C.) to facilitate formation of the reaction product. The requisite temperature and time needed to facilitate formation of the reaction product is variable and can easily be determined by one skilled in the art. The formation of the reaction produced can approximated by observing the dissolution of the thiadiazole compound, which is normally solid at room temperature. The formation of the reaction product can also be confirmed by Infrared Spectroscopy (IR) since shifts in absorption are observed when comparing the IR spectra for the individual components versus the IR spectra for the reaction product.

The thiadiazole compound and the poly(ether)glycol are preferable reacted in a molar ratio or the starting materials of at least 0.2:1, with a ratio of at least 0.4:1 being more preferred. However, for further improved extreme pressure properties an equimolar or an excess ratio of the thiadiazole compound can be used (e.g., a molar ratio of 1:1, 2:1 or greater).

In another embodiment the present invention provides an additive including a mon-substituted thiadiazole-glycol condensation adduct having formula (IV):

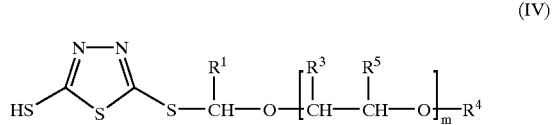

(IV)

in which $R^1$, $R^3$, $R^5$ and $R^4$ are independently selected from the above-described group of substituents for the reaction products. The number of repeating ether units "m" in the glycol moiety is 1 to 50, with 1 to 10 being preferred, and 1 to 3 being more preferred.

The thiadiazole-glycol adduct is prepared by reacting in a 1:1:1 molar ratio 2,5-dimercapto-1,3,4-thiadiazole (DMTD) with an aldehyde containing the substituent $R^1$ and a poly (ether)glycol as previously described for the reaction products. The components are mixed and heated for a sufficient amount of time to form the condensation adduct. Examples of the synthesis of similar condensation adducts with monohydric alcohols instead of glycols are disclosed in U.S. Pat. No. 5,194,621, which is incorporated herein by reference. These parameters can be easily modified by one skilled in the art.

The thiadiazole reaction products and adducts are incorporated as additives into lubricating compositions in an effective amount to impart adequate extreme pressure properties. In this context, adequate extreme pressure properties are considered to be passing a Timken Load of at least 40 pounds, with at least 50 pounds or greater being preferred. As will be apparent to one skilled in the art, the amount of the reaction products and adducts needed to provide adequate extreme pressure properties is variable. The additives can be added in a range from 0.1 to 10 weight percent of the lubricating composition, with at least 1 weight percent being preferred and at least 2 weight percent being more preferred.

In accordance with the present invention lubricating compositions suitable for incorporation of the extreme pressure additives include, but are not limited to, lubricating oils, engine oils and lubricating greases containing a major amount of base oil. A "major amount" in this context means that greater than 50 weight percent (wt. %) of the composition is base oil. Base oils to be used include, but are not limited to, napthenic, aromatic, parafinic, mineral, and synthetic oils. Representative synthetic oils include, but are not limited to, polysiloxanes, carboxylic acid esters and polyglycol ethers.

In a preferred embodiment, the lubricating composition is a grease which is prepared by adding to a base oil thickeners such as salts and complexes of fatty acid soaps, polyurea compounds, mixed and complex soaps of alkali metals, alkaline earth metals, aluminum, modified clays and quaternary ammonium bentonite complexes. Various other additives can be incorporated as desired.

The following non-limiting examples illustrate the synthesis of the thiadiazole-glycol reaction products and adducts, and their use as extreme pressure additives in lubricating compositions.

EXAMPLES

Thiadiazole-glycol reaction products were generally prepared by mixing in a specified mole ratio the thiadiazole compound with the structure of formula (I) with a poly (ether)glycol with structure of formula (III). The substituent "Z" was one of the following substituents: (1) a n-alkyl radical; (2) a thioalkyl radical; (3) an alpha bound succinate full ester, where the ester alkyl is represented by "G"; (4) an alkyloxy linkage having the structure of formula (II); or (5) a sodium salt.

Example 1

A thiadiazole-glycol reaction product was synthesized by adding to a three-neck flask 55.0 grams of mono-methylated DMTD and 35.1 grams of triethylene glycol monobutyl ether. The flask heated to 120° C. The monomethylated DMTD dissolved upon heating but recrystallized upon cooling on the sides of the flask. Additional triethylene glycol monobutyl ether was added until the monomethylated DMTD no longer recrystallized. A total of 126.0 grams of glycol was used. The reaction mixture was heated for approximately 4 hours from 110 to 130° C. Once the reaction mixture cooled, the liquid reaction product was filtered to remove any impurities. The structural characteristics of the reaction product (i.e., compound 1) are listed in Table 1.

Example 2–3

Following the general procedure described in Example 1, thiadiazole-glycol reaction products were prepared using a DMTD derivative having the "Z" substituents being alkyl and thioalkyl radicals (Z types-1 and 2, respectively), and poly(ether)glycols having the structure of formula (III). As in example 1, the reaction mixtures were heat to at 100° C. for at least 30 minutes. Once the reaction mixtures cooled, the liquid reaction products were filtered to remove any impurities. The structural characteristics of reaction products are listed in Table 1.

Example 4

A thiadiazole-glycol reaction product was prepared with "Z" being an alpha bound succinate fall ester (Z type-3). Approximately 129.1 grams of DMTD, 168.5 grams of butoxytriethylene glycol and 140.8 grams of diethylmaleate were added to a three-neck flask. The reaction mixture was heated from 100–120° C. for approximately 1½ hours. Once the reaction mixture cooled, the liquid reaction product was filtered to remove any impurities. The structural characteristics of the reaction product (i.e., compound 4) are listed in Table 1.

Example 5

A thiadiazole-glycol reaction product was prepared with the "Z" being an alkyloxy linkage (Z type-4) by adding to a three-neck flask 159.8 grams of a monobutoxymethyl derivative of DMTD and 68.5 grams of propylene glycol. The mixture was stirred at room temperature for approximately 30 minutes. The reaction product was filtered and the structural characteristics of the reaction product are listed in Table 1.

Examples 6–12

Following the general procedure of Example 5, thiadiazole-glycol reaction products were prepared. The structural characteristics of the reactions products are listed in Table 1.

Example 13

A thiadiazole-glycol reaction product was prepared following the general procedure of Example 4. The structural characteristics of the reaction product are listed in Table 1.

Example 14

A reaction product was prepared following the general procedure of Example 1. The structural characteristics of the reaction product are listed in Table 1.

Examples 15–17

Reaction products were prepared following the general procedure of Example 4. The structural characteristics of the reaction products are listed in Table 1.

Example 18

A reaction product was prepared following the general procedure of Example 1. The structural characteristics of the reaction product are listed in Table 1.

Example 19

A reaction product was prepared following the general procedure of Example 4. The structural characteristics of the reaction product are listed in Table 1.

Example 20

A reaction product was prepared following the general procedure of Example 5. The structural characteristics of the reaction product are listed in Table 1.

Examples 21–22

Reaction products were prepared following the general procedure of Example 4. The structural characteristics of the reaction products are listed in Table 1.

Example 23

A thiadiazole-glycol reaction product was prepared having the Z substituent being Sodium (Z type-5). Approximately 40.2 grams of DMTD monosodium half salt and 60.8 grams of ethylene glycol were added to a three-neck flask. The reaction mixture was heated for approximately 1½ hours at 110° C. to fully dissolve the DMTD reaction. Once the mixture cooled the liquid reaction product was filtered to remove any impurities. The structural characteristics of the reaction product (i.e., compound 23) are listed in Table 1.

minutes to remove any remaining water or unreacted starting material. Once the reaction mixture cooled, the liquid adduct was filtered to remove any impurities. The structural characteristics of the adduct (i.e., compound 24) are listed in Table 2.

Examples 25–36

Thiadiazole-glycol adducts were prepared following the general procedure of Example 24. As in Example 24, the reaction mixture were heated to at least 100° C. for at least 30 minutes. The structural characteristics of the adducts are listed in Table 2.

TABLE 2

| Adduct | $R^1$ | $R^3$ | M | $R^4$ |
|---|---|---|---|---|
| Compound 24 | H | H | 3 | Butyl |
| Compound 25 | 3-Heptyl | H | 3 | Butyl |
| Compound 26 | Methyl | H | 3 | Butyl |
| Compound 27 | Nonyl | H | 3 | Butyl |
| Compound 28 | Phenyl | H | 3 | Butyl |
| Compound 29 | H | H | 4 | H |
| Compound 30 | H | H | 3 | H |
| Compound 31 | 3-Heptyl | Methyl | 3 | Butyl |
| Compound 32 | 3-Heptyl | Methyl | 35 | Butyl |
| Compound 33 | Nonyl | H | 3 | Butyl |
| Compound 34 | Nonyl | H | 2 | nonylphenyl |
| Compound 35 | H | H | 1 | Butyl |
| Compound 36* | H | — | 0 | Butyl |

*Comparative adduct without the poly(ether) moiety.

Example 37

The synthesized reaction products and adducts were evaluated for 4-Ball Weld and Timken Load properties in

TABLE 1

| Reaction Product | Z Type | Carbon Atoms in Z | F | $R^3$ | n | $R^4$ | Thiadiazole: Glycol Ratio |
|---|---|---|---|---|---|---|---|
| Compound 1 | 1 | 1 | OH | H | 3 | Butyl | 2 |
| Compound 2 | 1 | 4 | OH | H | 3 | Butyl | 2 |
| Compound 3 | 2 | 8 | OH | H | 3 | Butyl | 2 |
| Compound 4 | 3 | 2 in G | OH | H | 3 | Butyl | 1 |
| Compound 5 | 4 | 4 in $R^2$, $R^1$ = H | OH | $CH_3$ | 1 | H | 0.75 |
| Compound 6 | 4 | 4 in $R^2$, $R^1$ = H | OH | H | 1 | Butyl | 2 |
| Compound 7 | 4 | 4 in $R^2$, $R^1$ = H | OH | H | 2 | Butyl | 2 |
| Compound 8 | 4 | 4 in $R^2$, $R^1$ = H | OH | H | 3 | Butyl | 2.6 |
| Compound 9 | 4 | 4 in $R^2$, $R^1$ = H | OH | $CH_3$/H | 52 | Butyl | 25.6 |
| Compound 10 | 4 | 4 in $R^2$, $R^1$ = H | OH | $CH_3$/H | 66 | Butyl | 33.3 |
| Compound 11[1] | 4 | 8 in $R^2$, $R^1$ = H | OH | H | 3 | Butyl | 2 |
| Compound 12 | 4 | 8 in $R^2$, $R^1$ = H | OH | H | 3 | Butyl | 1 |
| Compound 13 | 3 | 6 in G | OH | H | 3 | Butyl | 1 |
| Compound 14 | 2 | 12 | OH | H | 3 | Butyl | 0.87 |
| Compound 15 | 3 | 2 in G | OH | $CH_3$ | 1 | OH | 1 |
| Compound 16 | 3 | 2 in G | nonanoate | H | 3 | nonanoate | 2.1 |
| Compound 17 | 3 | 2 in G | OH | H | 2 | OH | 1.0 |
| Compound 18 | 3 | 4 | OH | H | 3 | Butyl | 2 |
| Compound 19 | 3 | 8 in G | OH | H | 3 | Butyl | 2 |
| Compound 20[2] | 4 | 4 in $R^2$, $R^1$ = H | OH | H | 3 | Butyl | 2 |
| Compound 21 | 3 | 8 in G | OH | H | 3 | Butyl | 1 |
| Compound 22 | 3 | 6 in G | OH | H | 3 | Butyl | 1 |
| Compound 23 | 5 | — | OH | H | 3 | H | 0.24 |

[1]Mixture was not heated since thiadiazole compound was a liquid at room temperature.
[2]Comparative example using 5-methylthio-2-butoxylmethyl-1,3,4-thiadiazole.

Example 24

A thiadiazole-glycol adduct was prepared by adding to a three-neck flask approximately 140.6 grams of DMTD, 183.6 grams of butoxytriethylene glycol and 29.5 grams of paraformaldehyde to provide a 1:1:1 molar ratio. The flask was attached to a Dean-Stark apparatus and was heated from 135 to 150° C. for approximately 1½ hours. After which the flask was placed under a vacuum for approximately 15 accordance with ASTM D-2596, and ASTM D-2509, respectively. The grease formulations were prepared using Lithium-12 hydroxystearate grease at varying weight percents (wt. %) of the additive dispersed therein. The results of the 4-Ball Weld and Timken Load tests are shown below in Table 3.

TABLE 3

| Reaction Product or Adduct | 4-Ball Weld (kgf) | | Timken Load (pounds) | | | | |
|---|---|---|---|---|---|---|---|
| | 1% | 2% | 1% | 2% | 3% | 4% | 5% |
| Compound 1 | | | | | | P60* | |
| Compound 3 | | | | P60* | | | |
| Compound 4 | | | | P60* | | | |
| Compound 5 | | | | P60* | | | |
| Compound 8 | 250 | 315 | 50 | 80 | | | |
| Compound 9 | | | | P60* | | | |
| Compound 10 | | | | P60* | | | |
| Compound 11 | 250 | 250 | 30 | 80 | | | |
| Compound 12 | 250 | 250 | 30 | 80 | | | |
| Compound 14 | | | | | | | P50* |
| Compound 15 | | | | | | | P50* |
| Compound 16 | | | | | | | P50* |
| Compound 17 | | | | | | | P50* |
| Compound 18 | | | | | | | P60* |
| Compound 20 | | | | | | 50 | 60 |
| Compound 21 | | | | | | | F50* |
| Compound 22 | | | | | | | F50* |
| Compound 23 | | | | | | | P50* |
| Compound 24 | | 315 | | | | | |
| Compound 25 | | 400 | | 70 | | | |
| Compound 26 | 250 | 315 | 70 | 80 | | | |
| Compound 27 | | 250 | | | | | |
| Compound 28 | | 315 | | | | | |
| Compound 29 | | 400 | | | | | |
| Compound 30 | | 400 | | | | | |
| Compound 31 | | | | 40 | | | |
| Compound 32 | | | | 40 | | | |
| Compound 35 | | | | | | | P50* |
| Compound 36 | | | F40* | F40* | | | |

*A discriminating test was run to determine EP performance at a predetermined load: a Pass ("P") or Fail ("F") at specified concentration (typically 5 wt. %) allowed for rapid evaluation of the reaction product/adduct.

Readily apparent from the data set forth in Table 3 is that the reaction products and adducts of the present invention provide good Timken Loads (i.e., Timken Loads greater than 35 lbs.) and 4-Ball Weld properties. For example, the grease formulation containing 1 wt. % of compound 8 exhibited a 4-Ball Weld value of 250 kilograms force (kgf) and a Timken Load of 50 lbs. Better yet, the grease formulation containing 1 wt. % of compound 25 exhibited a 4-Ball Weld value of 250 kilograms force (kgf) and a Timken Load of 70 lbs.

We claim:

1. An additive for use in lubricants comprising a reaction product of:

(A) a thiadiazole compound having formula (I):

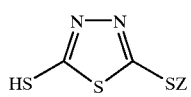

(I)

where Z is selected from the group consisting of a branched or straight chain $C_1$ to $C_{20}$ alkyl radical, a $C_1$ to $C_{20}$ thioalkyl radical, an alpha bound succinate half or full ester, wherein the ester alkyl is a $C_1$ to $C_5$ alkyl radical, an alkali metal, an alkyloxy linkage having formula (II):

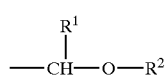

(II)

with $R^1$ being selected from the group consisting of hydrogen, a $C_1$ to $C_{20}$ branched or straight chain alkyl radical, a phenyl radical, a $C_1$ to $C_{20}$ branched or straight chain alkyl-substituted-phenyl radical, and combinations thereof and $R^2$ being selected from the group consisting of hydrogen, a $C_1$ to $C_{20}$ branched or straight chain alkyl radical, a phenyl radical, a $C_1$ to $C_{20}$ branched or straight chain alkyl-substituted-phenyl radical, and combinations thereof; and (B) a poly(ether)glycol having formula (III):

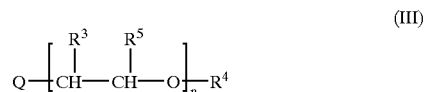

(III)

where Q is selected from the group consisting of a hydroxyl radical, a branched or straight chain $C_1$ to $C_{20}$ alkoxy radical, a branched or straight chain $C_1$ to $C_{20}$ alkylcarboxyl radical, a mono-substituted, di-substituted, or tri-substituted glycerol residue, hydrogen, or combination thereof; where $R^3$ and $R^5$ are selected from the group consisting of hydrogen and a methyl radical, where $R^4$ is selected from the group consisting of hydrogen, a branched or straight-chain a $C_1$ to $C_{20}$ alkyl radical, a phenyl radical, a $C_1$ to $C_8$ branched or straight chain alkyl-substituted-phenyl radical, a $C_1$ to $C_{20}$ branched or straight chain acyl radical, or combinations thereof; and where n is 1 to 300.

2. The additive of claim 1, wherein Z is $C_1$ to $C_8$ alkyl radical.

3. The additive of claim 1, wherein Z is $C_1$ to $C_8$ thioalkyl radical.

4. The additive of claim 1, wherein Z is the alkyloxy linkage where $R^1$ is hydrogen and $R^2$ is $C_1$ to $C_8$ alkyl radical.

5. The additive of claim 1, wherein Q is a hydroxyl radical.

6. The additive of claim 1, wherein Q is a $C_1$ to $C_{10}$ alkylcarboxyl radical.

7. The additive of claim 1, wherein $R^2$ is hydrogen.

8. The additive of claim 1, wherein $R^4$ is a $C_1$ to $C_8$ alkyl radical.

9. The additive of claim 1, wherein $R^4$ is a $C_1$ to $C_{10}$ acyl radical.

10. The additive of claim 1, wherein $R^3$ and $R^5$ are both hydrogen.

11. The additive of claim 1, wherein the thiadiazole compound and the poly(ether)glycol are reacted in a ratio of at least 0.2:1.

12. The additive of claim 11, wherein the thiadiazole compound and poly(ether)glycol are reacted in a ratio of at least 0.4:1.

13. The additive of claim 12, wherein the thiadiazole compound and poly(ether)glycol are reacted in a ratio at least 1:1.

14. The additive of claim 1, wherein n is from 1 to 150.

15. The additive of claim 13, wherein n is from 1 to 10.

16. An additive for use in lubricants, comprising a thiadiazole-glycol adduct having formula (IV):

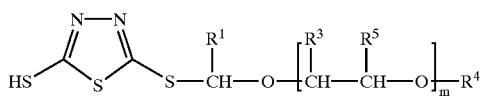

(IV)

where $R^1$ is selected from the group consisting of hydrogen, a branched or straight chain $C_1$ to $C_{20}$ alkyl radical, a phenyl radical, a branched or straight chain $C_1$ to $C_{20}$ alkylsubstituted-phenyl radical and combination thereof; where $R^3$ and $R^5$ are selected from the group consisting of hydrogen and a methyl radical; where $R^4$ is selected from the group consisting of hydrogen, a $C_1$ to $C_{20}$ branched or straight chain alkyl radical, a phenyl radical, a branched or straight chain $C_1$ to $C_{20}$ alkyl-substituted-phenyl radical, a branched or straight chain $C_1$ to $C_{20}$ acyl radical, and combinations thereof; and wherein m is from 1 to 50.

17. The additive of claim 15, wherein $R^1$ is a $C_1$ to $C_8$ alkyl radical.

18. The additive of claim 15, wherein $R^1$ is hydrogen.

19. The additive of claim 15, wherein $R^4$ is hydrogen.

20. The additive of claim 15, wherein $R^4$ is a $C_1$ to $C_8$ alkyl radical.

21. The additive of claim 15, wherein m is from 1 to 10.

22. The additive of claim 15, wherein m is 1 to 3.

23. A lubricating composition comprising a major amount of a base oil and an effective amount of the additive of claim 1.

24. The lubricating composition of claim 22, wherein the additive is at least 1 weight percent of the composition.

25. A lubricating composition comprising a major amount of a base oil and an effective amount of the additive of claim 15.

26. The lubricating composition of claim 24, wherein the additive is at least 1 weight percent of the composition.

* * * * *